United States Patent [19]

Speights

[11] Patent Number: 4,902,674
[45] Date of Patent: Feb. 20, 1990

[54] METHOD FOR INHIBITING THE GROWTH OF SALMONELLA

[75] Inventor: Robert M. Speights, Arvada, Colo.

[73] Assignee: Coors Biotech, Inc., Westminster, Colo.

[21] Appl. No.: 107,115

[22] Filed: Oct. 13, 1987

[51] Int. Cl.$^4$ .................. A61K 33/00; A61K 31/70
[52] U.S. Cl. .......................... 514/23; 424/92; 424/442; 426/2; 426/658; 514/54; 514/867
[58] Field of Search .............. 424/92, 442; 426/2, 426/658; 514/23, 54, 867

[56] References Cited

U.S. PATENT DOCUMENTS

| | | | |
|---|---|---|---|
| 3,701,714 | 10/1972 | Okada et al. | 435/97 |
| 3,703,440 | 11/1972 | Okada et al. | 435/97 |
| 3,728,132 | 4/1973 | Tsuyama et al. | 426/48 |
| 3,819,484 | 6/1974 | Okada et al. | 435/97 |
| 3,894,146 | 7/1975 | Tsuyama | 426/658 |
| 3,931,398 | 1/1976 | Gaffar et al. | 424/92 |
| 4,024,251 | 5/1977 | Maiese et al. | 435/886 |
| 4,133,875 | 1/1979 | Hillman | 424/93 |
| 4,160,026 | 7/1979 | Iwamatsu et al. | 435/84 |
| 4,276,379 | 6/1981 | Heady | 435/94 |
| 4,312,856 | 1/1982 | Korduner et al. | 424/145 |
| 4,316,894 | 2/1982 | Omoto et al. | 514/23 |
| 4,335,107 | 6/1982 | Snoeyenbos et al. | 426/61 |
| 4,374,154 | 2/1983 | Cole et al. | 426/565 |
| 4,401,662 | 8/1983 | Lormeau et al. | 514/56 |
| 4,435,389 | 3/1984 | Mutai et al. | 514/54 |
| 4,496,550 | 1/1985 | Lindahl et al. | 514/54 |
| 4,581,227 | 4/1986 | Kjelleberg et al. | 514/474 |
| 4,681,771 | 7/1987 | Adachi et al. | 426/658 |
| 4,689,226 | 8/1987 | Nurmi et al. | 426/2 |
| 4,693,898 | 9/1987 | Nakatomi et al. | 426/19 |
| 4,726,948 | 2/1988 | Prieels et al. | 514/867 |
| 4,734,402 | 3/1988 | Hashimoto et al. | 514/54 |
| 4,762,822 | 8/1988 | Ettinger | 514/23 |

FOREIGN PATENT DOCUMENTS

| | | |
|---|---|---|
| 0006695 | 1/1980 | European Pat. Off. . |
| 0133547 | 2/1985 | European Pat. Off. . |
| 0171026 | 2/1986 | European Pat. Off. . |
| 0188047 | 7/1986 | European Pat. Off. . |
| 1336002 | 11/1973 | United Kingdom . |
| 1352633 | 5/1974 | United Kingdom . |
| 1390065 | 4/1975 | United Kingdom . |
| 2072679 | 10/1981 | United Kingdom . |
| 2105338 | 3/1983 | United Kingdom . |
| 2179946 | 3/1987 | United Kingdom . |

OTHER PUBLICATIONS

"Nondigestibility of a New Sweetner, 'Neosugar,' in the Rat", Oku, et al. Journal of Nutrition, vol. 114, No. 9, pp. 1574–1581 (1984).

"Microbial Colonization Control of Chicken Intestine Using Defined Cultures", S. Stavric, Food Technology 41(7), Jul. 1987, pp. 93–98.

"Substrate Specificity of Fructosyl Transferase from Chicory Roots", Singh, et al., Phytochemistry, 1971, vol. 10, pp. 2037–2039.

"Sucrose: Sucrose Fructosyltransferase and Fructan: Fructan Fructosyltransferase from Allium Sepa", Phytochemistry, 1980, vol. 19, pp. 1017–1020.

"Production of Several Oligosaccharides from Sucrose by the Action of an Aspergillus Enzyme Preparation and Structural Studies of the Products", Kyoritsu Yacka Daigaku Kenkyu Nempe, vol. 20, 1975.

The Greeley (Colo.) Daily Tribune, "Sugar Stops Bacteria in Poultry", Apr. 12, 1989, p.C6.

The Difco Manual of Dehydrated Culture Media and Reagents, Ninth Edition, 1953, pp. 134–138.

The Merck Index, An Encyclopedia of Chemicals and Drugs, Ninth Edition, 1976, p. 842.

Breed et al., Bergey's Manual of Determinative Bacteriology (6th ed.), vol. 1, p. 503 (1948).

Bergey's Manual of Systematic Bacteriology, vol. 1, p. 415 (1984).

Gutnick et al., "Compounds Which Serve as the Sole Source of Carbon or Nitrogen for *Salmonella* Typhimurium LT-2", J. Bacteriol., vol. 100, p. 215 (1969).

Hidaka et al., "Effect of Fructo-oligosaccharides on Human Intestinal Flora" (1984) (Japanese Reference).

"USDA Promotes Lactose, D-Mannose to Prevent Salmonella in Chickens", Food Chemical News, p. 27 (Apr. 3, 1989).

"Milk Products Could Get Salmonella Boost", Feed Business Report, vol. 2, No. 4, (Apr. 1989).

Primary Examiner—Ronald W. Griffin
Attorney, Agent, or Firm—Sheridan, Ross & McIntosh

[57] ABSTRACT

A method and composition for the inhibition of growth of Salmonella is provided. The effective composition of the invention is a class of fructo-oligosaccharides which inhibit the growth of Salmonella. More particularly, the fructo-oligosaccharides are sucrose molecules having from 1 to 8 fructose residues. This class of sugars is exemplified by "Neosugar" which includes 1-kestose, nystose, and 1-fructofuranosylnystose. The present method includes contacting Salmonella with the effective composition and can include feeding it to a domestic food animal. The present composition includes the effective component and nutritive feed material.

23 Claims, No Drawings

METHOD FOR INHIBITING THE GROWTH OF SALMONELLA

FIELD OF THE INVENTION

The present invention relates generally to the inhibition of growth of Salmonella. More specifically, the invention relates to a method for inhibiting the growth of Salmonella in the intestines of food animals to prevent Salmonella infections in humans.

BACKGROUND OF THE INVENTION

Salmonella bacteria are well known human pathogens. The most common means of human infections is by ingestion of contaminated foods. Many species of Salmonella are recognized as common microflora in the intestines of food animals, such as poultry and beef.

Various compositions are known for treatment of Salmonella poisoning in humans. For example, chloramphenicol, ampicillin, and trimethoprim-sulfa, are known to be effective against Salmonella organisms. While such compositions are generally useful against Salmonella, the ideal method for controlling Salmonella poisoning is prevention of infection. Proper cleaning of meat and dairy products and thorough cooking can prevent human infection by Salmonella.

One embodiment of the present invention is a method for controlling Salmonella poisoning in humans by inhibiting the growth of Salmonella populations in food animals. In this manner, fewer organisms are present in the food animals, and therefore, the chance of transmission to humans is smaller. This method involves introducing an effective compound for the inhibition of growth of Salmonella to the intestinal tract of food animals.

Specific embodiments of the effective compound of the present method are produced by Meiji Seika Kaisha, Ltd. under the trade name "Neosugar". For example, in Oku et at., *Nondigestibility of a New Sweetener, "Neosugar," in the Rat*, J. of Nutrition, v. 114, No. 9, pp. 1575–81 (1984), Neosugar is described as a mixture of 1-kestose, nystose, and 1-fructofuranosyl nystose which was studied for digestibility in rats. See also U.S. Pat. No. 4,681,771 to Adachi, et al. (July 21, 1987), U.K. Pat. No. GB 2,072,679 and U.K. Pat. No. GB 2,150,338, owned by Meiji Seika, which discuss the use of Neosugar compositions as low-cariogenic and lowcalorie sweeteners.

Similar compounds are known for a variety of other uses. In European patent application No. 85300340.8, filed on 18 Jan. 1985, a process for preparing a compound termed "fructo-oligosaccharose" was disclosed. The process involves culturing an Aureo-bacidium species to produce the enzyme fructosyl-transferase. The culture medium is then contacted with sucrose to provide a substrate for the production of this fructo-oligosaccharose by the enzyme.

European patent application No. 84109126.7, Publication No. 0133547, describes an animal feed for preventing scours (diarrhea) which includes fructo-oligosaccharides produced by the action of fructosyl transferase on sucrose.

U.S. Pat. No. 4,496,550 to Lindahl, et al. (Jan. 29, 1985) and U.S. Pat. No. 4,401,662 to Lormeau, et al. (Aug. 30, 1983) discuss the use of mixtures of oligosaccharides to counteract or prevent coagulation of blood to prevent arterial thrombosis.

U.S. Pat. No. 3,701,714 to Shigetaka (Oct. 31, 1972) and U.S. Pat. No. 3,703,440 to Shigetaka (Nov. 21, 1972) discuss the use of oligosaccharides as the main constituent for use as a starch syrup. U.S. Pat. No. 3,728,132 to Tsuyama, et al. (Apr. 17, 1973) and U.S. Pat. No. 3,894,146 to Tsuyama (July 8, 1975), discuss the use of oligosaccharides as a low cariogenic sweetener.

U.S. Pat. No. 4,435,389 to Mutai, et al. (Mar. 6, 1984) discusses an oligosaccharide composition for promoting the growth of Bifidobacteria in human intestines. The oligosaccharide composition has a general formula of Gal-(gal)n-Glc, wherein "Gal" denotes a galactose residue, "Glc" a glucose residue, and "n" an integer of one to four. Bifidobacteria is a bacteria living in the human intestines with known beneficial physiological affects.

U.S. Pat. No. 4,160.026 to Iwamatsu (July 3, 1979) describes antibiotic oligosaccharides termed SF-1130-$x_1$ and SF-1130-$x_2$ which are produced by the fermentation of *Streptomyces myxogenes* SF-1130. Toxicity against a number of microorganisms, including Salmonella, as tested by formation of inhibition zones from paper discs impregnated with the compounds was disclosed. These substances are described as active antibiotic substances against gram-negative bacteria.

U.S. Pat. No. 4,316,894 to Omoto, et al. (Feb. 23, 1982) discloses a compound designated as SF-1130-$x_3$ having a disclosed utility as a drug for suppressing blood sugar elevations after ingesting starch and/or sugars and as a weak antibacterial compound. Although a chemical structure is not provided, antibacterial activity was demonstrated in *E. coli*. SF-1130-$x_3$ is described an an oligosaccharide and detailed chemical characterizations of the substance are provided. SF-1130-$x_3$ is produced by fermentation of Streptomyces bacteria.

In view of the above, a new method for inhibiting the growth of Salmonella is highly desirable. Such a method is useful for controlling or limiting the population of Salmonella in the intestines of food animals as a means for preventing human Salmonella infections.

SUMMARY OF THE INVENTION

The present invention includes a method and composition for inhibiting the growth of Salmonella. In the method, a composition including fructo-oligosaccharides is contacted with the Salmonella to inhibit growth.

The fructo-oligosaccharides are more specifically characterized as sucrose molecules having from 1 to 8 fructose residues. This class of compounds is exemplified by a product, Neosugar, which includes as components 1-kestose, nystose, and 1-fructofuranosylnystose.

A particular embodiment of the invention includes feeding the composition to a food animal to inhibit the growth of Salmonella in the intestines of the animal. A further embodiment includes feeding the composition to an animal having intestinal Salmonella which cannot ferment and intestinal microflora, such as Lactobacillus or Streptococcus, which can ferment the fructo-oligosaccharides of the composition. In this method, Salmonella are competitively inhibited by the enhanced growth of other bacteria.

Another aspect of the present invention is a feed composition for the inhibition of intestinal Salmonella in food animals. The composition has a nutritive component and a component which includes fructo-oligosaccharides in an amount effective to inhibit the growth of Salmonella.

DETAILED DESCRIPTION

One aspect of the present invention involves a method for inhibiting the growth of Salmonella. A particular application of the invention is the inhibition of Salmonella in the intestines of animals for the prevention of infection of humans who later ingest food products from the animals. Another aspect of the invention is a feed composition for the inhibition of intestinal Salmonella in food animals. Generally, the effective composition in the method and feed composition is a mixture of fructo-oligosaccharides which inhibits growth of species of Salmonella. It is believed that inhibition occurs due to the inability of Salmonella to ferment the effective composition. The effective composition and specific embodiments of the effective composition will be discussed in more detail below. However, for the present, all embodiments will be generally referred to as the "effective composition."

The method for inhibiting the growth of Salmonella includes contacting a population of Salmonella with the effective composition. It has been found that in the presence of the effective composition, with only minimal amounts of carbohydrate sources other than the effective composition available, Salmonella fermentation activity is limited. The fermentation which does occur is thought to be fermentation of small quantities of glucose or sucrose present in the medium. While not wishing to be bound by theory, it is believed that the lack of fermentation activity is due to the inability of Salmonella to bread down components of the effective composition into smaller sugar units. Therefore, according to this theory, in an environment where the effective composition is present, growth of Salmonella is inhibited by reduced carbohydrate availability. If the carbohydrate source of the environment consists primarily of the effective composition, inhibition is very strong. If the environment has other carbohydrate sources which can be used by Salmonella, inhibition occurs, but at a lower level.

The embodiment of the effective composition discussed above appears to inhibit growth of Salmonella due to the inability of the organism to ferment the effective composition. It should be noted, however, that other effective compositions may inhibit Salmonella growth by other mechanisms, e.g. toxicity. Such other compositions are specifically contemplated and are considered to be within the scope of the present invention.

A particular embodiment of the present method involves introducing the effective composition to the intestinal tract of a food animal. A wide variety of microflora are present in the intestines of all animals. In the intestines of many animals from which humans derive food, populations of Salmonella are present without any deleterious effects to the animals. However, transmission of a sufficient number of Salmonella organisms to a human can cause serious illness. By introducing the effective composition to the intestines of a food animal, the balance of intestinal microflora is shifted away from Salmonella in favor of other species of microflora. In this manner, the likelihood of transmission of Salmonella organisms to humans from food animals is reduced because the initial Salmonella population is smaller.

The present method is particularly effective when microflora which are not pathogenic to humans and which can ferment the effective composition are present in the intestines of the food animal. In such animals, growth of Salmonella is competitively inhibited by the enhanced growth of other forms of microflora. For example, it has been found that the effective composition can be fermented by Lactobacillus and Streptococcus. These microorganisms are commonly found in many food animals and will not cause human illness. Poultry are known to have Salmonella, Lactobacillus and Streptococcus populations in their intestines. By introducing the effective composition to poultry, the growth of non-pathogenic microflora is enhanced and the population of Salmonella decreases. The overall balance of microflora in the intestines of the poultry will be shifted in favor of bacteria not harmful to humans, Lactobacillus and Streptococcus. The likelihood of human infection by Salmonella is thereby decreased because the source population of Salmonella is reduced.

The effective composition of the present invention includes fructo-oligosaccharides which cannot be fermented by Salmonella. "Fructo-oligosaccharides", as used herein, refers to a trisaccharide having one or more additional fructose residues. This class includes mixtures of oligosaccharide molecules comprised of sucrose having from 1 to 8 fructose residues. The fructose residues are preferably attached by a beta 2-1 bond. The class is exemplified by the fructo-oligosaccharides in the Neosugar produced by Meiji Seika and as described in U.S. Pat. No. 4,681,771, which is incorporated by reference herein.

Neosugar is a mixture including 1-kestose, nystose, and 1-fructofuranosyl-nystose. Neosugar, as used herein, is more particularly defined as having between about 20% by weight and about 40% by weight 1-kestose, between about 20% by weight and about 55% be weight nystose, and between about 5% by weight and about 15% by weight 1-fructofuranosyl-nystose. The remaining portion of a Neosugar mixture can include between about 4% by weight and about 45% by weight of a mixture of glucose and sucrose. In one form, Neosugar G, the composition is a 75% syrup having between about 40% by weight and about 50% by weight of a mixture of glucose and sucrose, between about 20% by weight and about 30% by weight 1-kestose, between about 20% by weight and about 30% by weight nystose, and between about 2% by weight and about 8% by weight 1-fructofuranosyl-nystose. In another form, Neosugar P, the composition is either a 75% syrup or a powder having between about 2% by weight and about 6% by weight of a mixture of glucose and sucrose, between about 30% by weight and about 40% by weight 1-kestose, between about 45% by weight and about 55% by weight nystose, and between about 5% by weight and about 15% by weight 1-fructofuranosyl-nystose. The structures of 1-kestose, nystose, and 1-fructofuranosyl-nystose are provided below.

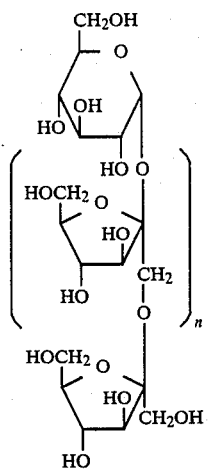

where:
n = 1 for 1-kestose
n = 2 for nystose
n = 3 for 1-fructofuranosylnystose

Neosugar can be produced by the action of fructosyl-transferase on sucrose to produce a mixture of 1-kestose, nystose, and 1-fructofuranosyl nystose. Neosugar G, for example, can be produced by subjecting the product of fructosyl-transferase activity to decoloration, filtration, desalting, and concentration. Neosugar G can be further purified with an ion exchange resin to produce Neosugar P. Although these methods produce mixtures of fructo-oligosaccharides, it is contemplated that the use of the pure compounds which are in Neosugar are within the scope of the invention.

Certain fungi, such as, Aspergillus and Aureobasidium are known to produce the enzyme fructosyltransferase. Fructosyl transferases which produce oligosaccharides are known to be produced by chicory plant and by onion plant. See Singh et al., *Substrate Specificity of Fructosyl Transferase From Chicory Roots*, Phytochemistry vol. 10, pp. 2037-39 (1971) and Henry et al., *Sucrose: Sucrose Fructosyltransferase and Fructan: Fructan Fructosyltransferase From Allium Cepa*, Phytochemistry vol. 19, pp. 1017-20 (1980).

In a preferred embodiment of the present method, the effective composition is fed to a food animal where the inhibition of the growth of intestinal Salmonella will occur. The preferred method of introduction is to mix the effective composition with nutritive feed material for the animal. It is contemplated, however, that the effective composition can either be mixed with the nutritive feed material or fed to the animal separately. In either embodiment, the effective composition must be provided in an amount effective to inhibit the growth of Salmonella. This amount will vary depending upon the size of the food animal. Poultry will require smaller quantities of the effective composition than, for example, beef to inhibit intestinal Salmonella. Effective amounts can readily be determined by experimentation.

In practice of the present method by feeding the effective composition to food animals to inhibit intestinal Salmonella populations, it is not necessary to practice the method for the entire life of the animal. The primary concern of the food industry is to prevent transmission of Salmonella to humans. Therefore, limiting the Salmonella population to a minimum by the present method just prior to slaughter of the food animal is sufficient to reduce the likelihood of transmission to the human population. In this manner, costs attendant to the present process can be minimized.

The feed composition of the present invention includes, as one component, the effective composition. The feed composition also includes some material which is nutritive for the animal to which the feed composition is fed. Typically, for most food animals, such as poultry or beef, the nutritive material is some type of grain product. It is contemplated that the majority of the feed composition can be nutritive material with the effective composition present in an amount sufficient to inhibit growth of intestinal Salmonella. Typically, the effective composition is present in an amount between about ¼% by weight and about 5% by weight and more preferably between about ¼% by weight and about 1% by weight.

The method and composition of the present invention can be used for inhibiting the growth of Salmonella in a wide variety of animals from which humans obtain food. Many such animals are known to have intestinal Salmonella populations, and therefore, can potentially contaminate any meat or dairy products consumed by humans. Accordingly, the present method and composition are contemplated for use with any type of food animal, including but not limited to, poultry, beef, pork, and lamb. The term "poultry" is meant to include, but not be limited to, chickens, ducks, turkeys, geese, quail, and rock cornish game hens.

The following experimental results are provided for purposes of illustration and are not intended to limit the scope of the invention. The bacterial strains in the following examples were obtained from Colorado Animal Research Enterprises, Inc., 6200 E. County Road 56, Ft. Collins, Colorado 80524.

EXPERIMENTAL

Example 1

A strain of *Salmonella typhimurium*, species source poultry, obtained from Lilly, No. 289-1 was tested for the ability to metabolize Neosugar P. This ability was measured by acid production as measured by Phenol Red Broth Base (PRB). Growth, as measured by turbidity, was also tested.

A fermentation medium of PRB (Difco) was prepared and sterilized according to manufacturer's instructions. PRB is a defined medium which lacks a carbohydrate source. If an added carbohydrate source, such as Neosugar P, is fermented, the medium turns yellow as a positive response due to acid formed by the fermentation. 5.0 ml of the PRB was dispensed into 10 test tubes. A 70% solution of Neosugar P was diluted by 1:7 in deionized water and filter sterilized. 0.5 ml of the diluted, sterile Neosugar P solution was aseptically added to individual PRB tubes to provide a 1.0% concentration of sugar in each tube. Five of the ten tubes were overlaid with mineral oil to simulate anaerobic conditions. After incubation at 37° C.±1° C., acid production and growth were measured at 24, 48, and 72 hours. The strain was also tested for viability on Tryptic-Soy (T-Soy) Agar plates and tested for presence of Salmonella on Salmonella-Shigella (SS) Agar plates. The results of these tests are provided in Table 1.

The symbol "w+" means "weak positive", "+" means "positive", "++" means "strong positive", "+++" means "strongest positive", and "−" means "no detectable positive response".

TABLE 1

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | w+ | − | − | + | + | ++ |
| 7* | w+ | − | − | + | + | ++ |
| 8* | w+ | − | − | + | + | ++ |
| 9* | w+ | − | − | + | + | ++ |
| 10* | w+ | − | − | + | + | ++ |

SS Agar - very good growth; yellow; some black colonies
T-Soy Agar - very good growth
*anaerobic

Example 2

A strain of *Salmonella typhimurium* from cattle, FDA No. 2952 was tested according to the procedure in Example 1. The results of these tests are provided in Table 2.

TABLE 2

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | w+ | − | − | + | + | ++ |
| 7* | w+ | − | − | + | + | ++ |
| 8* | w+ | − | − | + | + | ++ |
| 9* | w+ | − | − | + | + | ++ |
| 10* | w+ | − | − | + | + | ++ |

SS Agar - very good growth; yellow; some black colonies
T-Soy Agar - very good growth
*anaerobic

Example 3

A strain of *Salmonella typhimurium*, from cattle NVSL No. 82-4481, was tested according to the procedure in Example 1. The results of these tests are provided in Table 3.

TABLE 3

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | w+ | w+ | − | + | + | ++ |
| 7* | w+ | − | − | + | + | ++ |
| 8* | w+ | − | − | + | + | ++ |
| 9* | w+ | − | − | + | + | ++ |
| 10* | w+ | − | − | + | + | ++ |

SS Agar - good growth; yellow; black colonies
T-Soy Agar - very good growth
*anaerobic

Example 4

A strain of *Salmonella typhimurium* from swine, NVSL No. 83-31641-4807 was tested according to the procedure in Example 1. The results of these tests are provided in Table 4.

TABLE 4

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | w+ | w+ | − | + | + | ++ |
| 7* | w+ | w+ | − | + | + | ++ |
| 8* | w+ | − | − | + | + | ++ |
| 9* | w+ | − | − | + | + | ++ |
| 10* | w+ | − | − | + | + | ++ |

SS Agar - good growth; yellow; black colonies
T-Soy Agar - good growth
*anaerobic

Example 5

A strain *Salmonella typhimurium* from swine, NVSL No. 83-31296-4756 was tested according to the procedure in Example 1. The results of these tests are provided in Table 5.

TABLE 5

| Test Tube | S. typhimurium | | | | | |
|---|---|---|---|---|---|---|
| | Acid Formation | | | Growth | | |
| | 24 | 48 | 72 | 24 | 48 | 72 |
| 1 | w+ | − | − | + | + | ++ |
| 2 | − | w+ | − | + | + | ++ |
| 3 | w+ | − | − | + | + | ++ |
| 4 | w+ | − | − | + | + | ++ |
| 5 | − | − | − | + | + | ++ |
| 6* | w+ | w+ | − | + | + | ++ |
| 7* | w+ | w+ | − | + | + | ++ |
| 8* | w+ | − | − | + | + | ++ |
| 9* | w+ | − | − | + | + | ++ |
| 10* | w+ | − | − | + | + | ++ |

SS Agar - good growth; yellow; some black
T-Soy Agar - good growth
*anaerobic

Example 6

A strain of *Escherichia coli* from poultry, Pfizer No. B028, was tested according to the procedure in Example 1. The results of these tests are provided in Table 6.

TABLE 6

| Test Tube | E. coli | | | | | |
|---|---|---|---|---|---|---|
| | Acid Formation | | | Growth | | |
| | 24 | 48 | 72 | 24 | 48 | 72 |
| 1 | − | − | − | + | + | ++ |
| 2 | − | − | − | + | + | ++ |
| 3 | w+ | − | − | + | + | ++ |
| 4 | w+ | − | − | + | + | ++ |
| 5 | w+ | − | − | + | + | ++ |
| 6* | + | w+ | − | + | + | ++ |
| 7* | + | w+ | − | + | + | ++ |
| 8* | + | w+ | − | + | + | ++ |
| 9* | + | w+ | − | + | + | ++ |
| 10* | + | w+ | − | + | + | ++ |

SS Agar - single colony; black red
T-Soy Agar - good growth; 2-3 mm
*anaerobic

Example 7

A strain of *Escherichia coli* from poultry, NVSL No. 80-430 was tested according to the procedure in Example 1. The results of these tests are provided in Table 7.

TABLE 7

| Test Tube | E. coli Acid Formation | | | Growth | | |
|---|---|---|---|---|---|---|
| | 24 | 48 | 72 | 24 | 48 | 72 |
| 1 | w+ | − | − | + | + | ++ |
| 2 | w+ | − | − | + | + | ++ |
| 3 | w+ | − | − | + | + | ++ |
| 4 | w+ | − | − | + | + | ++ |
| 5 | w+ | − | − | + | + | ++ |
| 6* | ++ | + | w+ | + | + | ++ |
| 7* | ++ | + | w+ | + | + | ++ |
| 8* | ++ | + | w+ | + | + | ++ |
| 9* | ++ | + | w+ | + | + | ++ |
| 10* | ++ | + | w+ | + | + | ++ |

SS Agar - no growth
T-Soy Agar - good growth; 2 mm; motile
*anaerobic

Example 8

A strain of *Escherichia coli* from cattle, NVSL No. 85-688 was tested according to the procedure in Example 1. The results of these tests are provided in Table 8.

TABLE 8

| Test Tube | E. coli Acid Formation | | | Growth | | |
|---|---|---|---|---|---|---|
| | 24 | 48 | 72 | 24 | 48 | 72 |
| 1 | w+ | − | − | + | + | +++ |
| 2 | w+ | − | − | + | + | +++ |
| 3 | w+ | − | − | + | + | +++ |
| 4 | w+ | − | − | + | + | +++ |
| 5 | w+ | − | − | + | + | +++ |
| 6* | + | + | w+ | + | + | +++ |
| 7* | + | + | w+ | + | + | +++ |
| 8* | + | + | w+ | + | + | +++ |
| 9* | + | + | w+ | + | + | +++ |
| 10* | + | + | w+ | + | + | +++ |

SS Agar - single colony; black red
T-Soy Agar - good growth; 2–3 mm
*anaerobic

Example 9

A strain of *Escherichia coli* from swine, University of Guelp, G491 was tested according to the procedure in Example 1. The results of these tests are provided in Table 9.

TABLE 9

| Test Tube | E. coli Acid Formation | | | Growth | | |
|---|---|---|---|---|---|---|
| | 24 | 48 | 72 | 24 | 48 | 72 |
| 1 | w+ | w+ | +++ | + | + | +++ |
| 2 | w+ | w+ | +++ | + | + | +++ |
| 3 | w+ | w+ | +++ | + | + | +++ |
| 4 | w+ | w+ | +++ | + | + | +++ |
| 5 | w+ | w+ | +++ | + | + | +++ |
| 6* | ++ | ++ | +++ | + | + | +++ |
| 7* | ++ | ++ | +++ | + | + | +++ |
| 8* | ++ | ++ | +++ | + | + | +++ |
| 9* | ++ | ++ | +++ | + | + | +++ |
| 10* | ++ | ++ | +++ | + | + | +++ |

SS Agar - selected colonies; pink/red
T-Soy Agar - good growth; 2–3 mm
*anaerobic

Example 10

A strain of *Escherichia coli* from swine, NVSL No. 85-746 was tested according to the procedure in Example 1. The results of these tests are provided in Table 10.

TABLE 10

| Test Tube | E. coli Acid Formation | | | Growth | | |
|---|---|---|---|---|---|---|
| | 24 | 48 | 72 | 24 | 48 | 72 |
| 1 | ++ | ++ | +++ | ++ | ++ | +++ |
| 2 | ++ | ++ | +++ | ++ | ++ | +++ |
| 3 | ++ | ++ | +++ | ++ | ++ | +++ |
| 4 | ++ | ++ | +++ | ++ | ++ | +++ |
| 5 | ++ | ++ | +++ | ++ | ++ | +++ |
| 6* | +++ | +++ | +++ | ++ | ++ | +++ |
| 7* | +++ | +++ | +++ | ++ | ++ | +++ |
| 8* | +++ | +++ | +++ | ++ | ++ | +++ |
| 9* | +++ | +++ | +++ | ++ | ++ | +++ |
| 10* | +++ | +++ | +++ | ++ | ++ | +++ |

SS Agar - no growth
T-Soy Agar - very good growth; 3 mm; motile
*anaerobic

Example 11

A strain of *Streptococcus faecalis* obtained from the Center for Disease Control, STR-11 was tested according to the procedure in Example 1. The results of these tests are provided in Table 11.

TABLE 11

| Test Tube | Streptococcus faecalis Acid Formation | | | Growth | | |
|---|---|---|---|---|---|---|
| | 24 | 48 | 72 | 24 | 48 | 72 |
| 1 | ++ | +++ | +++ | + | ++ | +++ |
| 2 | ++ | +++ | +++ | + | ++ | +++ |
| 3 | ++ | +++ | +++ | + | ++ | +++ |
| 4 | ++ | +++ | +++ | + | ++ | +++ |
| 5 | ++ | +++ | +++ | + | ++ | +++ |
| 6* | ++ | +++ | +++ | + | ++ | +++ |
| 7* | ++ | +++ | +++ | + | ++ | +++ |
| 8* | ++ | +++ | +++ | + | ++ | +++ |
| 9* | ++ | +++ | +++ | + | ++ | +++ |
| 10* | ++ | +++ | +++ | + | ++ | +++ |

SS Agar - no growth
T-Soy Agar - small white colonies
*anaerobic

Example 12

A strain of *Streptococcus faecalis* obtained from Colorado State University Microbiology Department Culture Collection was tested according to the procedure in Example 1. The results of these tests are provided in Table 12.

TABLE 12

| Test Tube | Streptococcus faecalis Acid Formation | | | Growth | | |
|---|---|---|---|---|---|---|
| | 24 | 48 | 72 | 24 | 48 | 72 |
| 1 | ++ | +++ | +++ | + | ++ | +++ |
| 2 | ++ | +++ | +++ | + | ++ | +++ |
| 3 | ++ | +++ | +++ | + | ++ | +++ |
| 4 | ++ | +++ | +++ | + | ++ | +++ |
| 5 | ++ | +++ | +++ | + | ++ | +++ |
| 6* | ++ | +++ | +++ | + | ++ | +++ |
| 7* | ++ | +++ | +++ | + | ++ | +++ |
| 8* | ++ | +++ | +++ | + | ++ | +++ |
| 9* | ++ | +++ | +++ | + | ++ | +++ |
| 10* | ++ | +++ | +++ | + | ++ | +++ |

SS Agar - no growth
T-Soy Agar - small white colonies; 1 mm
*anaerobic

Example 13

A strain of *Lactobacillus plantarum*, obtained from Colorado State University Microbiology Department Culture Collection was tested according to the procedure in Example 1. The results of these tests are provided in Table 13.

TABLE 13

| Test Tube | Lactobacillus plantarum | | | | | |
|---|---|---|---|---|---|---|
| | Acid Formation | | | Growth | | |
| | 24 | 48 | 72 | 24 | 48 | 72 |
| 1 | + | ++ | +++ | w+ | + | ++ |
| 2 | + | ++ | +++ | w+ | + | ++ |
| 3 | + | ++ | +++ | w+ | + | ++ |
| 4 | + | ++ | +++ | w+ | + | ++ |
| 5 | − | ++ | +++ | − | + | ++ |
| 6* | + | ++ | +++ | w+ | + | ++ |
| 7* | + | ++ | +++ | w+ | + | ++ |
| 8* | + | ++ | +++ | w+ | + | ++ |
| 9* | + | ++ | +++ | w+ | + | ++ |
| 10* | + | ++ | +++ | w+ | + | ++ |

SS Agar - no growth
T-Soy Agar - poor growth; very small colonies
*anaerobic

From the above experiments, it can be seen that the Salmonella strains exhibited little fermentation activity as measured by acid formation. While all strains showed some initial "weak positive" results, this initial activity likely indicates fermentation of the glucose and sucrose in the Neosugar composition.

All of the Salmonella strains showed consistent moderate growth as measured by turbidity. The lack of fermentation while growth occurred indicates that the Neosugar was not the carbon source for any growth of Salmonella. It appears, therefore, that some other carbon source, such as, for example, amino acids, in the PRB was used by Salmonella. The fact that Salmonella is able to grow in the presence of Neosugar indicates that, although the organism is unable to ferment the fructo-oligosaccharides in Neosugar, these compositions are not toxic to Salmonella at the concentrations in these tests.

While various embodiments of the present invention have been described in detail, it is apparent that modifications and adaptations of those embodiments will occur to those skilled in the art. However, it is to be expressly understood that such modifications and adaptations are within the scope of the present invention, as set forth in the following claims.

What is claimed is:

1. A method for inhibiting the growth of Salmonella, comprising contacting said Salmonella with a composition comprising a fructo-oligosaccharide.

2. A method as claimed in claim 1, wherein said fructo-oligosaccharide is a sucrose molecule having from 1 to 8 fructose residues attached to the sucrose molecule.

3. A method as claimed in claim 1, wherein said composition includes compounds selected from the group consisting of 1-kestose, nystose, 1-fructofuranosylnystose and mixtures thereof.

4. A method as claimed in claim 3, wherein said composition comprises between about 20% by weight and about 40% by weight 1-kestose, between about 20% by weight and about 50% by weight nystose, and between about 5% by weight and about 15% by weight 1-fructofuranosyl-nystose.

5. A method as claimed in claim 3, wherein said composition further comprises glucose and sucrose.

6. A method as claimed in claim 1, wherein said step of contacting comprises feeding said composition to an animal having intestinal Salmonella.

7. A method as claimed in claim 6, wherein said animal further has an intestinal population of microflora capable of fermenting said fructo-oligosaccharide.

8. A method as claimed in claim 7, wherein said microflora capable of fermenting said fructo-oligosaccharide comprise populations selected from the group consisting of Lactobacillus, Streptococcus, and mixed populations thereof.

9. A method for competitively inhibiting the growth of Salmonella in the presence of microflora comprising populations selected from the group consisting of Lactobacillus, Streptococcus, and mixed populations thereof comprising contacting a composition comprising a fructo-oligosaccharide to a mixed population of Salmonella and microflora comprising populations selected from the group consisting of Lactobacillus, Streptococcus, and mixed populations thereof.

10. A method as claimed in claim 9, wherein said fructo-oligosaccharide is a sucrose molecule having from 1 to 8 fructose residues attached to the sucrose molecule.

11. A method as claimed in claim 9, wherein said composition comprises a material selected from the group consisting of 1-kestose, nystose, 1-fructofuranosylnystose and mixtures thereof.

12. A method as claimed in claim 11, wherein said composition comprises between about 20% by weight and about 40% by weight 1-kestose, between about 20% by weight and about 50% by weight nystose, and between about 50% by weight and about 15% by weight 1-fructofuranosyl-nystose.

13. A method as claimed in claim 9, wherein said composition further comprises glucose and sucrose.

14. A method as claimed in claim 9, wherein said mixed population of Salmonella and Lactobacillus occurs in the intestines of a food animal.

15. A method as claimed in claim 14 wherein said food animal is a chicken.

16. A method as claimed in claim 14, wherein said step of contacting comprises feeding said composition to said food animal.

17. A method for selectively inhibiting the growth of intestinal Salmonella in the presence of intestinal microflora other than Salmonella in a food animal, comprising feeding said food animal a composition comprising a compound which is fermented by said intestinal microflora other than Salmonella at a rate competitively greater than the rate at which said compound is fermented by Salmonella.

18. A method as claimed in claim 17, wherein said food animal is poultry.

19. A method as claimed in claim 17, wherein said food animal is a chicken.

20. A method as claimed in claim 17, wherein said microflora other than Salmonella comprise a population of microflora selected from the group consisting of Lactobacillus, Streptococcus, and mixed populations thereof.

21. A method as claimed in claim 17, wherein said compound is a saccharide.

22. A method as claimed in claim 17, wherein said compound is selected from the group consisting of monosaccharides, disaccharides and oligosaccharides.

23. A method as claimed in claim 17, wherein said compound is selected from the group consisting of lactose and mannose.

* * * * *

UNITED STATES PATENT AND TRADEMARK OFFICE
CERTIFICATE OF CORRECTION

PATENT NO. : 4,902,674

DATED : February 20, 1990

INVENTOR(S) : SPEIGHTS et al.

It is certified that error appears in the above-identified patent and that said Letters Patent is hereby corrected as shown below:

Cover page, patent heading, Item No. [19], after inventor's name "Speights", insert -- et al. --.

Cover page, Item No. [75], after "Inventor: Robert M. Speights, Arvada, Colo.", insert -- Peter J. Perna, Boulder, Colo. --.

Cover page, right-hand column, line 32, delete "Food" in Roman type and insert -- Food -- (in italicized type) therefor.

Column 1, line 47, delete "lowcalorie" and insert -- low-calorie -- therefor.

Column 1, line 50, delete "patent application" and insert -- Patent Application -- therefor.

Column 1, line 58, delete "patent application" and insert -- Patent Application -- therefor.

Column 2, line 17, delete "4,160.026" and insert -- 4,160,026 -- therefor.

UNITED STATES PATENT AND TRADEMARK OFFICE
CERTIFICATE OF CORRECTION

PATENT NO. : 4,902,674

DATED : February 20, 1990

INVENTOR(S) : Speights, et al

It is certified that error appears in the above-identified patent and that said Letters Patent is hereby corrected as shown below:

Column 3, line 31, delete "bread" and insert --break-- therefor.

Column 4, line 34, delete "be" and insert --by-- therefor.

Signed and Sealed this

Fourth Day of June, 1991

Attest:

HARRY F. MANBECK, JR.

Attesting Officer

Commissioner of Patents and Trademarks